United States Patent
Lilley et al.

(10) Patent No.: US 11,198,912 B2
(45) Date of Patent: Dec. 14, 2021

(54) BIOMARKERS FOR THE DIAGNOSIS OF LUNG CANCERS

(71) Applicant: Liquid Lung DX, Fairfield, CT (US)

(72) Inventors: Patrick Lilley, Aliso Viejo, CA (US); Martin J. Keiser, III, Fairfield, CT (US)

(73) Assignee: Liquid Lung DX, Fairfield, CT (US)

( * ) Notice: Subject to any disclaimer, the term of this patent is extended or adjusted under 35 U.S.C. 154(b) by 0 days.

(21) Appl. No.: 17/003,775

(22) Filed: Aug. 26, 2020

(65) Prior Publication Data

US 2021/0102261 A1  Apr. 8, 2021

Related U.S. Application Data

(60) Provisional application No. 62/902,243, filed on Sep. 19, 2019, provisional application No. 62/893,088, filed on Aug. 28, 2019, provisional application No. 62/891,943, filed on Aug. 26, 2019.

(51) Int. Cl.
  *C12Q 1/6886* (2018.01)

(52) U.S. Cl.
  CPC ...... *C12Q 1/6886* (2013.01); *C12Q 2600/118* (2013.01); *C12Q 2600/158* (2013.01); *C12Q 2600/178* (2013.01)

(58) Field of Classification Search
  None
  See application file for complete search history.

(56) References Cited

U.S. PATENT DOCUMENTS

| 2012/0004116 A1* | 1/2012 | Tsao | G16B 40/00 506/7 |
| 2014/0170242 A1* | 6/2014 | Wagner | C12Q 1/6886 424/649 |
| 2015/0315643 A1* | 11/2015 | O'Garra | C12Q 1/6886 506/2 |
| 2020/0255902 A1* | 8/2020 | Lisanti | G01N 33/57407 |

* cited by examiner

*Primary Examiner* — Carla J Myers
(74) *Attorney, Agent, or Firm* — Entralta P.C.; James F. Fleming; Peter D. Weinstein

(57) ABSTRACT

Embodiments of the invention include a system and method of using biomarkers in the diagnosis of lung cancer. A subject can be screened for lung cancer based on expression of specific mRNAs, miRNAs or the detection of a nucleic acid, protein, peptide or other biological molecule in blood, serum or plasma. Embodiments include 29 specific miRNAs for use as biomarkers to screen or distinguish healthy individuals from individuals affected with the disease, including a lung cancer, along with 81 additional nucleic acids, proteins or peptides for use as biomarkers to screen or distinguish healthy individuals from individuals affected with the disease, including a lung cancer. Levels of more than one of the mRNAs, miRNAs or proteins can be scored and compared to one or more threshold values to diagnose or determine the prognosis of lung cancer. Embodiments also include a kit for screening healthy subjects from subjects affected with the disease.

16 Claims, 1 Drawing Sheet

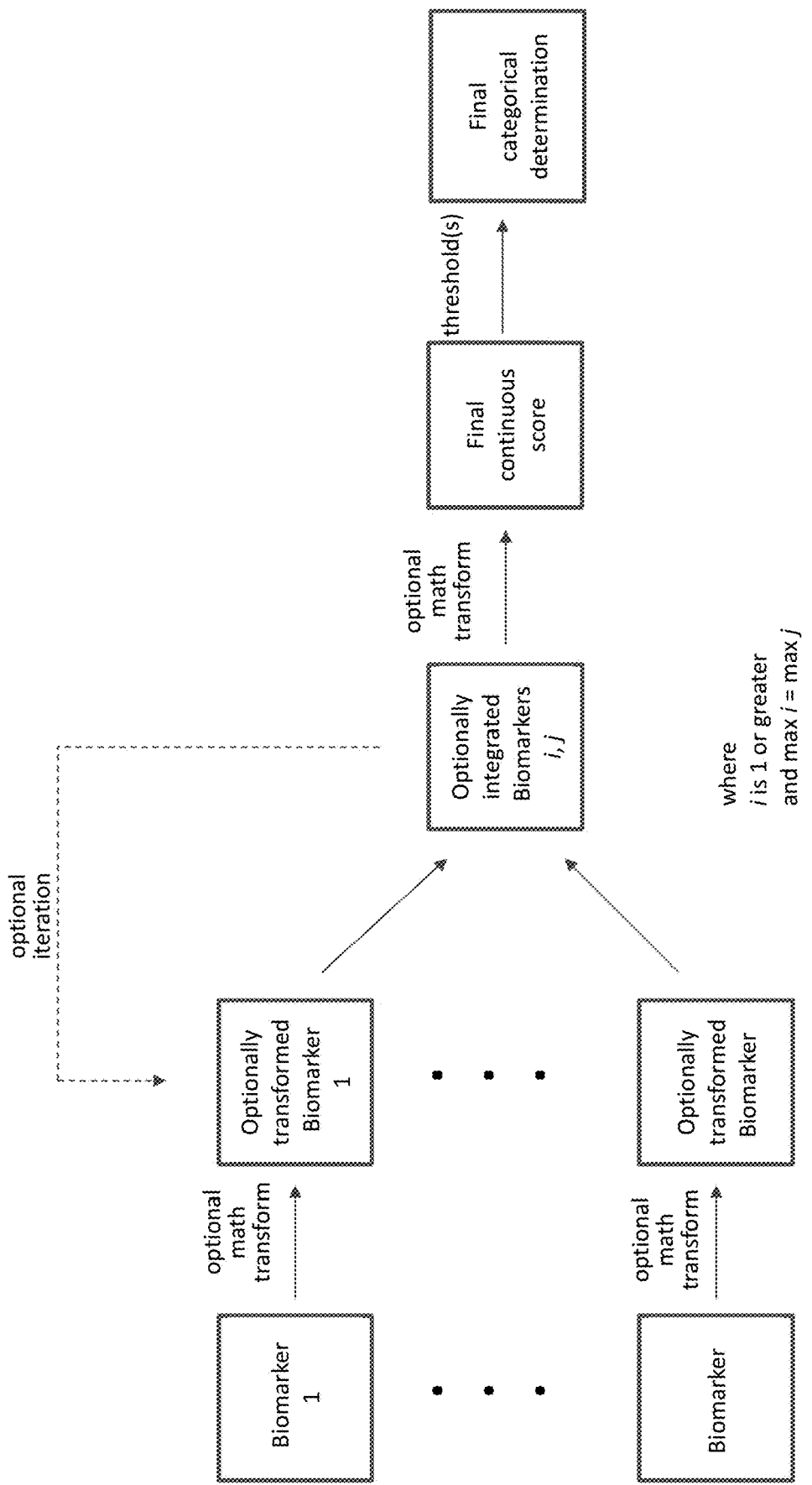

BIOMARKERS FOR THE DIAGNOSIS OF LUNG CANCERS

FIELD OF THE INVENTION

The invention relates to the diagnosis of disease using biomarkers, and more specifically, to a system and method of diagnosing adenocarcinoma based on specific miRNAs or other nucleotide or polypeptide hybridization that identify altered expression levels.

BACKGROUND

Lung cancer, also known as lung carcinoma, is a malignant lung tumor characterized by uncontrolled cell growth in tissues of the lung. This growth can spread beyond the lung by the process of metastasis into nearby tissue or other parts of the body. Subtypes of lung cancer include adenocarcinoma lung cancer, squamous cell lung cancer and small cell lung cancer. Treatment for lung cancer differs according to the subtype of cancer.

Adenocarcinoma is a type of cancerous tumor that can occur in several parts of the body. It is defined as neoplasia of epithelial tissue that has glandular origin, glandular characteristics, or both. Nearly 40% of lung cancers are adenocarcinomas, which usually originates in peripheral lung tissue. This cancer is usually seen peripherally in the lungs, as opposed to small cell lung cancer and squamous cell lung cancer, which both tend to be more centrally located.

Most cases of lung adenocarcinoma (also referred to as non-small cell lung cancer or NSCLC) are associated with smoking. However, it is the most common form of lung cancer among non-smokers. Lung adenocarcinoma is one of the tumor types with the highest number of mutations. Common somatic mutations in lung adenocarcinoma affect many oncogenes and tumor suppressor genes.

Squamous cell lung cancer begins in the squamous cells—thin, flat cells that line the inside of the airways in the lungs. About 30% of all lung cancers are classified as squamous cell lung cancer. It is more strongly associated with smoking than any other type of non-small cell lung cancer. Other risk factors for squamous cell lung cancer include age, family history, and exposure to secondhand smoke, mineral and metal dust, asbestos, or radon. Squamous cell carcinoma often spreads (i.e. metastasizes) to other parts of the body because of the constant flow of fluids (e.g. blood and lymph) through the lungs.

Small cell lung cancer accounts for about 15% of all lung cancers and is found most often in people with a smoking history. Small cell lung cancer usually starts in the bronchi, the major airways in the center of the chest that lead to the lungs, although about it can also be found in the periphery of the lungs. Small cell lung cancer is a type of neuroendocrine tumor which can grow and spread rapidly.

Lung cancer can be detected on chest radiographs and computed tomography (CT) scans. The diagnosis is typically confirmed with a biopsy of the suspect tissue. Biopsy can also determine the subtype of lung cancer. Most patients who suffer from lung cancer, including adenocarcinoma, are diagnosed at late stages of the disease when the survival late is low. If the cancer has spread to distant parts of the body (i.e. metastatic lung cancer) the five-year survival rate is approximately 6%. The survival rate is longer if the cancer is detected in its early stages when more treatment options are available. Accordingly, there is a need for methods to allow for the detection of the disease in its early stages before metastasis.

A microRNA (miRNA) is a small non-coding RNA molecule that functions in RNA silencing and post-transcriptional regulation of gene expression. miRNAs are evolutionary conserved and endogenously expressed, small non-coding RNAs of 20-25 nucleotides in size. miRNAs function via base-pairing with complementary sequences within mRNA molecules. As a result, these mRNA molecules are silenced, by one or more processes: cleavage of the mRNA strand into two pieces, destabilization of the mRNA through shortening of its poly(A) tail and/or less efficient translation of the mRNA into proteins. miRNAs have been implicated with critical functions in cellular development, differentiation, proliferation, and apoptosis.

Recent studies have provided evidence of abnormal expression patterns of miRNAs in patients with cancers. This presents the possibility of their potential use as diagnostic and prognostic biomarkers. Other biomolecules or markers that can also be used to identify changes in the genomic sequence of genes that have an association with the onset of a lung cancer include short nucleotide polymorphisms, also known as a snp or snps. Additionally, changes in the genomic sequence of a gene, including a single or multiple point mutations in a gene or a mutation in a region of a gene can also be identified and associated with the onset of a lung cancer.

However, diagnostic assays have been ineffective or unreliable in part because of the variability of expression of biomarkers. Moreover, conventional assays typically rely on a single molecular marker. Because of these limitations, diagnostic methods have not enabled reliable predictions of the presence of cancer or tumor progression. Thus, there is a need for the identification of alternative molecular markers that overcome these limitations.

SUMMARY OF THE INVENTION

The following summary is provided to facilitate an understanding of some of the innovative features unique to the disclosed embodiment and is not intended to be a full description. A full appreciation of the various aspects of the embodiments disclosed herein can be gained by taking into consideration the entire specification, claims and abstract as a whole.

The invention relates to a method for diagnosing a lung cancer, or a predisposition to a lung cancer in a patient comprising steps of (a) determining in a sample of a patient the amount of at least one biomarker from Table 1 or Table 2 and (b) comparing the amount of the at least one biomarker with a reference. Particular biomarkers can identify the type of lung cancer as one of squamous cell lung cancer, non-small cell lung cancer, large cell lung cancer, small cell lung cancer and adenocarcinoma lung cancer. The method can use additional biomedical information in addition to biomarkers.

Embodiments include a method of diagnosing a lung cancer or determining a prognosis of a subject with a lung cancer, the method comprising the steps of (a) measuring expression levels of at least two miRNAs in a test sample from the subject, (b) receiving the expression levels with a computer, (c) compiling the expression levels to yield a score, and (d) comparing the score to one or more threshold values to diagnose or determine the prognosis of lung cancer.

Embodiments also include a method of diagnosing a lung cancer or determining a prognosis of a subject with a lung cancer, the method comprising the steps of (a) measuring expression levels of at least two nucleic acids, proteins or peptides in a test sample from the subject, (b) receiving the expression levels with a computer, (c) compiling the expression levels to yield a score, and (d) comparing the score to one or more threshold values to diagnose or determine the prognosis of lung cancer.

The methods described herein can use one or more of the biomarkers that include, but are not limited to, mRNA and protein probes set forth in Table 1 and miRNAs set forth in Table 2. Embodiments include methods that use one or more biomarkers to identify (1) lung cancer in a patient. Embodiments also include methods that use one or more biomarkers to identify (2) small cell lung cancer (SCLC), (3) non-small cell lung cancer (NSCLC, not adenocarcinoma), (4) NSCLC Adenocarcinoma, (5) NSCLC squamous cell carcinoma and (6) NSCLC large cell undifferentiated in a patient. Particular biomarkers can be used to identify the type of cancer, as referenced in Table 3.

Additional embodiments include a system and method of detection and diagnosis of lung cancer. Embodiments also include a system and method of detection and diagnosis of lung cancer that is not identifiable by conventional methods (e.g. imaging and biopsy). Embodiments further include a system and method of distinguishing between lung cancers, including (SCLC, NSCLC, NSCLC adenocarcinoma, NSCLC squamous carcinoma and NSCLC large cell undifferentiated). The systems and methods can utilize biomarkers along with additional biomedical information of a patient. The biomarkers include those set forth in Table 1 and Table 2 below.

The methods described herein can use one or more mRNAs or proteins transcribed/translated from the following genes: TCTN3, DENND1A, FOS, MFSD11, PRPS1L1, F13A1, KLHL24, SSRP1, DDX24, KIF1B, RRP7A, MICALL1, C9 or f16, SEPHS1, DMAC2L, ITGA2B, PURA, PAFAH1B3, PDXK, ARAF, TBCD, UBA1, EED, PARVB, RCN2, PGAP3, REX1BD (619 or f60), MED27, PIK3IP1, YTHDF3, BHMT2, ASF1A, ANXA8, ETFA, NMT1, EPHB3, KIF3C, LOH11CR2A (VWA5A), SLC48A1, MAPKAPK5-AS1, PLA2G4B, CALHM2, SENP5, SIDT2, R3HDM4, MARK4, SSH3, ATOH1, AXIN2, TAS2R13, PCDHB1, VWA7, TRIM49, CNTD2, TSHZ2, CDHR5, KIF26B, PADI4, TRIM36, LGI2, KCNMB4, TTTY14, ELAVL3, PAGE4, PER2, ZNF142, CD4, CCS, NELL2, RNF44, KLHL21, DNAJB12, CDC123, GNAI3, TRADD and THRA.

The methods described herein can use one or more of the following miRNAs: hsa-miR-1204, hsa-miR-141-3p, hsa-miR-1827, hsa-miR-938, hsa-miR-125b-5p, hsa-miR-297, hsa-miR-10a-5p, hsa-miR-145-5p, hsa-miR-217, hsa-miR-3185, hsa-miR-21-5p, hsa-miR-363-3p, hsa-miR-631, hsa-miR-655, hsa-miR-1245b-5p, hsa-miR-369-3p, hsa-miR-875-3p, hsa-miR-105-5p, hsa-miR-1253, hsa-miR-1285-3p, hsa-miR-512-5p, hsa-miR-550b-3p, hsa-miR-571, hsa-miR-935, hsa-miR-145-5p, hsa-miR-3185, hsa-miR-1285-3p, hsa-miR-125b-5p and hsa-miR-550b-3p.

Embodiments include a method of diagnosing cancer or determining a prognosis of a subject with cancer (such as lung adenocarcinoma), comprising steps of a) measuring the expression level of at least one miRNA in a test sample from plasma of the subject; b) comparing the expression level of the at least one miRNA in the test sample to a level in a base sample; and c) diagnosing or determining the prognosis of cancer based on altered expression the miRNA in the test sample.

Embodiments further include a method of diagnosing cancer or determining a prognosis of a subject with cancer (such as lung adenocarcinoma), comprising steps of a) measuring the expression level of at least one miRNA in a test sample from plasma of the subject; b) comparing the expression level of the at least one miRNA in the test sample to a level in a base sample; and c) diagnosing or determining the prognosis of cancer based on altered expression the miRNA in the test sample.

Embodiments also include a method of diagnosing cancer or determining a prognosis of a test subject with cancer (such as lung adenocarcinoma), comprising steps of: a) measuring expression levels of two or more miRNAs in buffy coat obtained from blood from subjects with cancer; b) measuring expression levels of the two or more miRNAs in buffy coat obtained from blood from samples from healthy subjects; c) comparing the expression levels of the two or more miRNAs in the buffy coat obtained from blood from samples from the subjects with cancer to the levels in the plasma samples from the healthy subjects; d) identifying miRNAs that have altered levels of expression in the buffy coat obtained from blood from samples from the subjects with cancer; e) creating a biomarker fingerprint from the miRNAs with altered levels of expression; and f) diagnosing or determining the prognosis of cancer in the test subject by comparing of levels of miRNAs from plasma of the test subject to those in the biomarker fingerprint.

Embodiments also include a diagnostic kit for diagnosing cancer, wherein the kit comprises a plurality of nucleic acid molecules, each nucleic acid molecule encoding a miRNA sequence. The nucleic acid molecules identify variations in expression levels of one or more miRNAs in a plasma sample from a test subject. The expression levels of one or more miRNAs can represent a nucleic acid expression fingerprint that is indicative for the presence of cancer. The kit can identify one or more target cells exhibiting lung cancer in plasma from a test subject.

Embodiments also include a method for identifying one or more mammalian target cells exhibiting cancer comprising steps of: a) collecting a blood sample from a test subject; b) hybridizing at least one nucleic acid molecule biomarker encoding a miRNA sequence to a portion of the blood sample; c) quantifying the miRNA expression; d) determining the expression levels of a plurality of nucleic acid molecules, each nucleic acid molecule encoding a miRNA sequence; e) determining the expression levels of the plurality of nucleic acid molecules in one or more control cells; and f) identifying from the plurality of nucleic acid molecules one or more nucleic acid molecules that are differentially expressed in the target and control cells by comparing the respective expression levels obtained in steps (d) and (e). The one or more differentially expressed nucleic acid molecules together can represent a nucleic acid expression biomarker fingerprint that is indicative of the presence of lung cancer.

BRIEF DESCRIPTION OF THE FIGURES

FIG. 1 depicts a method of combining results from biomarkers to achieve a final categorical determination.

DEFINITIONS

Reference in this specification to "one embodiment/aspect" or "an embodiment/aspect" means that a particular feature, structure, or characteristic described in connection with the embodiment/aspect is included in at least one embodiment/aspect of the disclosure. The use of the phrase "in one embodiment/aspect" or "in another embodiment/aspect" in various places in the specification are not necessarily all referring to the same embodiment/aspect, nor are separate or alternative embodiments/aspects mutually exclusive of other embodiments/aspects. Moreover, various features are described which may be exhibited by some embodiments/aspects and not by others. Similarly, various requirements are described which may be requirements for some embodiments/aspects but not other embodiments/aspects. Embodiment and aspect can be in certain instances be used interchangeably.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

As applicable, the terms "about" or "generally", as used herein in the specification and appended claims, and unless otherwise indicated, means a margin of +/−20%. Also, as applicable, the term "substantially" as used herein in the specification and appended claims, unless otherwise indicated, means a margin of +/−10%. It is to be appreciated that not all uses of the above terms are quantifiable such that the referenced ranges can be applied.

The term "algorithm" refers to a specific set of instructions or a definite list of well-defined instructions for carrying out a procedure, typically proceeding through a well-defined series of successive states, and eventually terminating in an end-state.

The term "biomarker" refers generally to a DNA, RNA, protein, carbohydrate, or glycolipid-based molecular marker, the expression or presence of which in a subject's sample can be detected by standard methods (or methods disclosed herein) and is predictive or prognostic of the effective responsiveness or sensitivity of a mammalians subject with cancer. Biomarkers may be present in a test sample but absent in a control sample, absent in a test sample but present in a control sample, or the amount or of biomarker can differ between a test sample and a control sample. For example, genetic biomarkers assessed (e.g., specific mutations and/or SNPs) can be present in such a sample, but not in a control sample, or certain biomarkers are seropositive in the sample, but seronegative in a control sample. Also, optionally, expression of such a biomarker may be determined to be higher than that observed for a control sample. The terms "marker" and "biomarker" are used herein interchangeably.

The amount of the biomarker can be measured in a test sample and compared to the "normal control level," utilizing techniques such as reference limits, discrimination limits, or risk defining thresholds to define cutoff points and abnormal values for lung disease. The normal control level means the level of one or more biomarkers or combined biomarker indices typically found in a subject not suffering from lung disease. Such normal control level and cutoff points can vary based on whether a biomarker is used alone or in a formula combining with other biomarkers into an index. Alternatively, the normal control level can be a database of biomarker patterns from previously tested subjects who did not experience lung cancer over a clinically relevant time.

After selection of a set of biomarkers, well-known techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, or kernel principal components analysis algorithms, or other mathematical and statistical methods can be used to develop a formula for calculation of a risk score. A selected population of individuals is used, where historical information is available regarding the values of biomarkers in the population and their clinical outcomes. To calculate a risk score for a given individual, biomarker values are obtained from one or more samples collected from the individual and used as input data.

Tests to measure biomarkers and biomarker panels can be implemented on a variety of diagnostic test systems. Diagnostic test systems are apparatuses that typically include means for obtaining test results from biological samples. Examples of such means include modules that automate the testing (e.g., biochemical, immunological, nucleic acid detection assays). Some diagnostic test systems are designed to handle multiple biological samples and can be programmed to run the same or different tests on each sample. Diagnostic test systems typically include means for collecting, storing and/or tracking test results for each sample, usually in a data structure or database. Examples include well-known physical and electronic data storage devices (e.g., hard drives, flash memory, magnetic tape, paper printouts). It is also typical for diagnostic test systems to include means for reporting test results. Examples of reporting means include visible display, a link to a data structure or database, or a printer. The reporting means can be a data link to send test results to an external device, such as a data structure, data base, visual display, or printer.

As used herein, "additional biomedical information" refers to one or more evaluations of an individual, other than using any of the biomarkers described herein, that are associated with lung cancer risk. "Additional biomedical information" includes any of the following: physical descriptors of an individual, physical descriptors of a pulmonary nodule observed by CT imaging, the height and/or weight of an individual, the gender of an individual, the ethnicity of an individual, smoking history, occupational history, exposure to known carcinogens (e.g., exposure to any of asbestos, radon gas, chemicals, smoke from fires, and air pollution, which can include emissions from stationary or mobile sources such as industrial/factory or auto/marine/aircraft emissions), exposure to second-hand smoke, family history of lung cancer (or other cancer), the presence of pulmonary nodules, size of nodules, location of nodules, morphology of nodules (e.g., as observed through CT imaging, ground glass opacity (GGO), solid, non-solid), edge characteristics of the nodule (e.g., smooth, lobulated, sharp and smooth, spiculated, infiltrating), and the like. Smoking history is usually quantified in terms of "pack years", which refers to the number of years a person has smoked multiplied by the average number of packs smoked per day. For example, a person who has smoked, on average, one pack of cigarettes per day for 35 years is referred to as having 35 pack years of smoking history. Additional biomedical information can be obtained from an individual using routine techniques known in the art, such as from the individual themselves by use of a routine patient questionnaire or health history questionnaire, etc., or from a medical practitioner, etc. Alternately, additional biomedical information can be obtained from routine imaging techniques, including CT imaging (e.g., low-dose CT imaging) and X-ray. Testing of biomarker levels in combination with an evaluation of any additional biomedical information may, for example, improve sensitivity, specificity, and/or AUC for detecting lung cancer (or other lung cancer-related uses) as compared to biomarker testing alone or evaluating any particular item of additional biomedical information alone (e.g., CT imaging alone).

The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., lung cancer samples and normal or control samples). ROC curves are useful for plotting the performance of a particular feature (e.g., any of the biomarkers described herein and/or any item of additional biomedical information) in distinguishing between two populations (e.g., cases having lung cancer and controls without lung cancer). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

As used herein, "detecting" or "determining" with respect to a biomarker value includes the use of both the instrument required to observe and record a signal corresponding to a biomarker value and the material/s required to generate that signal. In various embodiments, the biomarker value is detected using any suitable method, including fluorescence, chemiluminescence, surface plasmon resonance, surface acoustic waves, mass spectrometry, infrared spectroscopy, Raman spectroscopy, atomic force microscopy, scanning tunneling microscopy, electrochemical detection methods, nuclear magnetic resonance, quantum dots, and the like.

The term "fingerprint," "disease fingerprint," or "biomarker signature" refers to a plurality or pattern of biomarkers that have elevated or reduced levels in a subject with disease. A fingerprint can be generated by comparing subjects with the disease to healthy subjects and used for screening/diagnosis of the disease.

The term "miRNA" or "micro RNA," "miRNA biomarkers," or "MicroRNAs" refers to small endogenous RNA molecules that can be used as serum diagnostic biomarkers for diseases including cancers. They are small non-coding RNA molecules (containing about 22 nucleotides) found in plants, animals and some viruses, that function in RNA silencing and post-transcriptional regulation of gene expression. miRNAs function via base-pairing with complementary sequences within mRNA molecules. As a result, these mRNA molecules are silenced, by one or more of the following processes: (1) Cleavage of the mRNA strand into two pieces, (2) Destabilization of the mRNA through shortening of its poly(A) tail, and (3) Less efficient translation of the mRNA into proteins by ribosomes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid and derivatives thereof can include cysteine, cystine, a cysteine sulfoxide, allicin, selenocysteine, methionine, isoleucine, leucine, lysine, phenylalanine, threonine, tryptophan, 5-hydroxytryptophan, valine, arginine, histidine, alanine, asparagine, aspartate, glutamate, glutamine, glycine, proline, serine, tyrosine, ornithine, carnosine, citrulline, carnitine, ornithine, theanine, and taurine.

The proteins and peptides described herein can have amino acid substitutions which do not alter the activity of the proteins or peptides (H. Neurath, R. L. Hill, The Proteins, Academic Press, New York, 1979). In one embodiment, these substitutions are "conservative" amino acid substitutions. The most commonly occurring substitutions are Ala/Ser, Val/Ile, Asp/Glu, Thr/Ser, Ala/Gly, Ala/Thr, Ser/Asn, Ala/Val, Ser/Gly, Ala/Pro, Lys/Arg, Asp/Asn, Leu/Ile, Leu/Val, Ala/Glu and Asp/Gly, in both directions.

As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Analogue as used herein denotes a peptide, polypeptide, or protein sequence which differs from a reference peptide, polypeptide, or protein sequence. Such differences may be the addition, deletion, or substitution of amino acids, phosphorylation, sulfation, acrylation, glycosylation, methylation, farnesylation, acetylation, amidation, and the like, the use of non-natural amino acid structures, or other such modifications as known in the art.

The term "medicament" refers to an active drug to treat cancer, such as adenocarcinoma, or the signs or symptoms or side effects of cancer.

The term "plasma" or "blood plasma" refers to the liquid portion of the blood that carries cells and proteins throughout the body. Plasma can be separated from the blood by spinning a tube of fresh blood containing an anticoagulant in a centrifuge until the blood cells fall to the bottom of the tube.

The term "PCR" or "polymerase chain reaction" refers to a common method used to make many copies of a specific DNA segment. Variations of the technique can be used to determine the presence and amount of one or more miRNAs in a sample. For example, a hydrolysis probe-based stem-loop quantitative reverse-transcription PCR (RT-qPCR) assay can be conducted to confirm and/or quantify the concentrations of selected miRNAs in serum samples from patients and controls.

The term "sample" refers to a biological sample obtained from an individual, body fluid, body tissue, cell line, tissue culture, or other source. Body fluids are, for example, lymph, sera, whole fresh blood, peripheral blood mononuclear cells, frozen whole blood, plasma (including fresh or frozen), urine, saliva, semen, synovial fluid and spinal fluid. Samples also include synovial tissue, skin, hair follicle, and bone marrow. Methods for obtaining tissue biopsies and body fluids from mammals are well known in the art.

The term "subject" or "patient" refers to any single animal, more preferably a mammal (including such non-human animals as, for example, dogs, cats, horses, rabbits, zoo animals, cows, pigs, sheep, and non-human primates) for which treatment is desired. Most preferably, the patient herein is a human.

The term "prognosis" refers to the forecast or likely outcome of a disease. As used herein, it refers to the probable outcome of liver disease, including whether the disease (e.g. lung cancer) will respond to treatment or mitigation efforts and/or the likelihood that the disease will progress.

"Optional" or "optionally" as used herein means that the subsequently described circumstance may or may not occur, so that the description includes instances where the circumstance occurs and instances where it does not.

The notation "SEQ ID NO:1" when used in a calculation is a value representing an amount of SEQ ID NO: 1 (i.e., an amount of an mRNA sequence comprising SEQ ID NO: 1) present in a sample. As can be appreciated, the notation can include other numerical representations.

Other technical terms used herein have their ordinary meaning in the art that they are used, as exemplified by a variety of technical dictionaries. The particular values and configurations discussed in these non-limiting examples can be varied and are cited merely to illustrate at least one embodiment and are not intended to limit the scope thereof.

DETAILED DESCRIPTION OF THE INVENTION

It is to be understood that both the foregoing general description and the following detailed description are exemplary and explanatory and are intended to provide further explanation of the subject technology as claimed. Additional features and advantages of the subject technology are set forth in the description below, and in part will be apparent from the description, or may be learned by practice of the subject technology. The advantages of the subject technology will be realized and attained by the structure particularly pointed out in the written description and claims hereof.

A microRNA (miRNA) is a small non-coding RNA molecule that functions in RNA silencing and post-transcriptional regulation of gene expression. Recent studies have demonstrated the presence of miRNAs in circulating blood and their potential for use as biomarkers in the diagnosis of various diseases. Specifically, efforts have proposed their use as biomarkers for early detection of cancers such as lung adenocarcinoma. Studies have demonstrated the potential of miRNA expression profiling in the diagnosis and prognosis of human lung cancer. Specific miRNAs are aberrantly expressed in malignant tissues as compared to nonmalignant lung tissue. Thus, such miRNAs can provide insights into cellular processes involved in the malignant transformation and progression of cancer.

Conventional methods of diagnosing early stages of lung cancer are generally unreliable. Chest x-rays and imaging tests diagnose lung cancer at advance stages. Biopsies are invasive and can be prone to error as they rely on subjective observations. The inventors have discovered differences in mRNA expression between healthy patients and those with lung cancer. Specific mRNAs are aberrantly expressed in diseased lungs as compared to healthy lungs. Specific miRNAs are also expressed at different levels in diseased and healthy lungs. The mRNAs/miRNAs can be detected in the blood, serum or plasma of patients. Thus, the present invention is based in part on the finding that liver disease can be reliably identified and different subtypes of liver disease can be distinguished based on particular mRNA/miRNA expression profiles with high sensitivity and specificity.

The present invention is based on the finding that lung cancer can be reliably identified and different subtypes of lung cancer can be discriminated based on particular miRNA expression profiles with high sensitivity and specificity. The expression of biomarkers typically includes both up- and down-regulated levels of miRNAs. However, some useful biomarkers will not have altered levels of expression. Biomarkers can be used as normalizers for batch effects or other technical variation in the sample handling, sample prep, sample extraction, biomarker measurement, instrument data processing, etc. Such biomarkers may or may not be indicative of cancer (in other words some normalizers also carry diagnostic information but others are just used to adjust for technical variation in biomarker measurement).

Embodiments include a set of biomarkers for diagnosis, prognosis and/or therapy of lung cancer. The methods described herein can include the combined measurement of at least two mRNA/miRNA/protein/peptide biomarkers and/or fragments of protein biomarkers referenced in Table 1 and Table 2 from human serum, plasma or a derivative of blood, or blood itself.

Embodiments also include a set of diagnostic markers or a molecular fingerprint, for quick and reliable identification and/or treatment of cells exhibiting or having a predisposition to develop different subtypes of lung cancer. Embodiments further include methods of diagnosing cancer based on specific miRNAs that have altered expression levels. While individual miRNAs can be monitored, the invention includes 29 miRNAs of particular value as biomarkers to screen or distinguish healthy individuals from individuals affected with disease. The miRNAs of particular interest include: hsa-miR-1204, hsa-miR-141-3p, hsa-miR-1827, hsa-miR-938, hsa-miR-125b-5p, hsa-miR-297, hsa-miR-10a-5p, hsa-miR-145-5p, hsa-miR-217, hsa-miR-3185, hsa-miR-21-5p, hsa-miR-363-3p, hsa-miR-63, hsa-miR-655, hsa-miR-1245b-5p, hsa-miR-369-3p, hsa-miR-875-3p, hsa-miR-105-5p, hsa-miR-1253, hsa-miR-1285-3p, hsa-miR-512-5p, hsa-miR-550b-3p, hsa-miR-571, hsa-miR-935, hsa-miR-145-5p, hsa-miR-3185, hsa-miR-1285-3p, hsa-miR-125b-5p and hsa-miR-550b-3p.

The methods and materials can be used for assessing subjects (e.g., human patients) for cancer such as lung adenocarcinoma. For example, embodiments include materials and methods for using identifiable markers to assist clinicians in assessing adenocarcinoma disease activity, assessing the likelihood of response and outcomes of therapy, and predicting long-term disease outcomes. Further, subjects with adenocarcinoma can be diagnosed based on the presence of certain diagnostic indicators in plasma from the subject. The technology provides diagnostic methods for predicting and/or prognosticating the effectiveness of treatment. In particular, the subject technology concerns the diagnosis of adenocarcinoma based on one or more combinations of markers.

Multiple miRNA biomarkers can be used from a single serum sample taken from a subject. According to some embodiments, multiple biomarkers are assessed and measured from different samples taken from the patient. According to some embodiments, the subject technology is used for a kit for predicting, diagnosing or monitoring responsiveness of a cancer treatment or therapy, wherein the kit is calibrated to measure marker levels in a sample from the patient.

According to some embodiments, the amount of biomarkers can be determined by using, for example, a reagent that specifically binds with the biomarker protein or a fragment thereof, (e.g., an antibody, a fragment of an antibody, or an antibody derivative). The level of expression can be determined using a method common in the art such as proteomics, flow cytometry, immunocytochemistry, immunohistochemistry, enzyme-linked immunosorbent assay, multichannel enzyme linked immunosorbent assay, and variations thereof. The expression level of a biomarker in the biological sample can also be determined by detecting the level of expression of a transcribed biomarker polynucleotide or fragment thereof encoded by a biomarker gene, which may be cDNA, mRNA or heterogeneous nuclear RNA (hnRNA). The step of detecting can include amplifying the transcribed biomarker polynucleotide, and can use the method of quantitative reverse transcriptase polymerase chain reaction. The expression level of a biomarker can be assessed by detecting the presence of the transcribed biomarker polynucleotide or a fragment thereof in a sample with a probe which anneals with the transcribed biomarker polynucleotide or fragment thereof under stringent hybridization conditions.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfite, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel.

In some embodiments, a microprocessor is part of a system for determining the presence of one or more miRNA or miRNAs (labeled herein as hsa-miR or has-miRs) associated with a cancer; generating standard curves; determining a specificity and/or sensitivity of an assay or marker; calculating an ROC curve; sequence analysis; all as described herein or is known in the art.

In some embodiments, a microprocessor is part of a system for determining the amount, such as concentration, of one or more miRNA or miRNAs (labeled herein as hsa-miR or has-miRs) associated with a cancer; generating standard curves; determining a specificity and/or sensitivity of an assay or marker; calculating an ROC curve; sequence analysis; all as described herein or is known in the art. The amount of one or more miRNA or miRNAs can be determined by abundance, measured per mole or millimole. The amount of miRNA or miRNAs can be determined by fluorescence, other measurement using an optical signal or other measurement known to one of skill to measure an miRNA or miRNAs.

In some embodiments, a microprocessor or computer uses methylation state data in an algorithm to predict a type or site of a cancer.

In some embodiments, a microprocessor or computer uses an algorithm to measure the amount of an miRNA or miRNAs. The algorithm can include, but are not limited to a mathematical interaction between a marker measurement or a mathematical transform of a marker measurement. The mathematical interaction and/or mathematical transform can be presented in a linear, nonlinear, discontinuous or discrete manner.

In some embodiments, a software or hardware component receives the results of multiple assays and determines a single value result to report to a user that indicates a cancer risk based on the results of the multiple assays. Related embodiments calculate a risk factor based on a mathematical combination (e.g., a weighted combination, a linear combination) of the results from multiple assays as disclosed herein.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, memory stick, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C #, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device. All such components, computers, and systems described herein as associated with the technology may be logical or virtual.

It is also envisioned that embodiments could be accomplished as computer signals embodied in a carrier wave, as well as signals (e.g., electrical and optical) propagated through a transmission medium. Thus, the various types of information discussed above could be formatted in a structure, such as a data structure, and transmitted as an electrical signal through a transmission medium or stored on a computer readable medium.

In some embodiments, the disclosure provides a system for predicting progression of a lung cancer. In another embodiment a lung cancer is a squamous cell lung cancer (e.g. non-small cell lung squamous cell lung cancer or non-small cell lung large cell undifferentiated lung cancer), a non-small cell non-adenocarcinoma lung cancer, a non-small cell lung cancer, a large cell lung cancer, a small cell lung cancer and/or an adenocarcinoma lung cancer. In an embodiment, a lung cancer, including any of the aforementioned lung cancers can be identified and the lung cancer predicted in an individual, the system comprising: an apparatus configured to determine expression levels of nucleic acids, proteins, peptides or other molecule from a biological sample taken from the individual; and hardware logic designed or configured to perform operations comprising: (a) receiving expression levels of a collection of signature genes from a biological sample taken from said individual, wherein said collection of signature genes comprises at least two genes selected from the group consisting of the sequences set forth in Table 1 or the mi-RNAs set forth in Table 2.

Information relevant to the patient's diagnosis include, but are not limited to, age, ethnicity, tumor localization, pertinent past medical history related to co-morbidity, other oncological history, family history for cancer, physical exam findings, radiological findings, biopsy date, biopsy result, types of operation performed (radical retropubic or radical perineal prostatectomy), neoadjuvant therapy (i.e. chemotherapy, hormones), adjuvant or salvage radiotherapy, hormonal therapy, local vs. distant disease recurrence and survival outcome. These clinical variables may be included in the predictive model in various embodiments.

Once a biomarker or biomarker panel is selected, a method for diagnosing an individual that may be suffering from a lung cancer. In an embodiment, a biomarker or biomarker panel is selected, a method for diagnosing an individual that may be suffering from a lung cancer, including squamous cell lung cancer (e.g. non-small cell lung squamous cell lung cancer or non-small cell lung large cell undifferentiated lung cancer), non-small cell non-adenocarcinoma lung cancer, non-small cell lung cancer, large cell lung cancer, small cell lung cancer and/or adenocarcinoma lung cancer and can comprise one or more of the following steps: 1) collect or otherwise obtain a biological sample; 2) perform an analytical method to detect and measure the biomarker or biomarkers in the panel in the biological sample; 3) perform any data normalization or standardization required for the method used to collect biomarker values; 4) calculate a biomarker score; 5) combine the biomarker scores to obtain a total diagnostic score; and 6) report the individual's diagnostic score. This method of diagnosis can be conducted using a computer and software programs for analysis of data collected from nucleic acid, protein, peptide or other biological molecules. In this approach, the diagnostic score may be a single number determined from the sum of all the marker calculations that is compared to a preset threshold value that is an indication of the presence or absence of disease. Or the diagnostic score may be a series of bars that each represent a biomarker value and the pattern of the responses may be compared to a pre-set pattern for determination of the presence or absence of disease.

For both DNA and RNA, the nucleic acid can be isolated from plasma or blood sample. The DNA or RNA can be extracellular or extracted from a cell in the plasma or blood sample. The DNA or RNA can also be extracted from a cellular biopsy, including from a tumor, including, a solid tumor in the lung.

For a protein or peptide or other biological molecule, such can be isolated from plasma or a blood sample. The protein or peptide or other biological molecule can be extracellular or extracted from a cell in the plasma or a blood sample. The protein or peptide or other biological molecule can also be extracted from a cellular biopsy, including from a tumor, including, a solid tumor in the lung.

It is also noted that many of the structures, materials, and acts recited herein can be recited as means for performing a function or step for performing a function. Therefore, it should be understood that such language is entitled to cover all such structures, materials, or acts disclosed within this specification and their equivalents, including the matter incorporated by reference.

The lung cancer, including squamous cell lung cancer (e.g. non-small cell lung squamous cell lung cancer or non-small cell lung large cell undifferentiated lung cancer), non-small cell non-adenocarcinoma lung cancer, non-small cell lung cancer, large cell lung cancer, small cell lung cancer and/or adenocarcinoma lung cancer biomarker analysis system can provide functions and operations to complete data analysis, such as data gathering, processing, analysis, reporting and/or diagnosis. For example, in one embodiment, the computer system can execute the computer program that may receive, store, search, analyze, and report information relating to the adenocarcinoma biomarkers. The computer program may comprise multiple modules performing various functions or operations, such as a processing module for processing raw data and generating supplemental data and an analysis module for analyzing raw data and supplemental data to generate an adenocarcinoma status and/or diagnosis. Diagnosing adenocarcinoma status may comprise generating or collecting any other information, including additional biomedical information, regarding the condition of the individual relative to the disease, identifying whether further tests may be desirable, or otherwise evaluating the health status of the individual.

The lung cancer, including squamous cell lung cancer (e.g. non-small cell lung squamous cell lung cancer or non-small cell lung large cell undifferentiated lung cancer), non-small cell non-adenocarcinoma lung cancer, non-small cell lung cancer, large cell lung cancer, small cell lung cancer and/or adenocarcinoma lung cancer biomarker analysis system can provide functions and operations to complete data analysis, such as data gathering, processing, analysis, reporting and/or diagnosis. For example, in one embodiment, the computer system can execute the computer program that may receive, store, search, analyze, and report information relating to the lung cancer biomarkers. The computer program may comprise multiple modules performing various functions or operations, such as a processing module for processing raw data and generating supplemental data and an analysis module for analyzing raw data and supplemental data to generate a lung cancer status and/or diagnosis. Diagnosing lung cancer status may comprise generating or collecting any other information, including additional biomedical information, regarding the condition of the individual relative to the disease, identifying whether further tests may be desirable, or otherwise evaluating the health status of the individual.

As used herein, a "computer program product" refers to an organized set of instructions in the form of natural or programming language statements that are contained on a physical media of any nature (e.g., written, electronic, magnetic, optical or otherwise) and that may be used with a computer or other automated data processing system. Such programming language statements, when executed by a computer or data processing system, cause the computer or data processing system to act in accordance with the particular content of the statements. Computer program products include without limitation: programs in source and object code and/or test or data libraries embedded in a computer readable medium. Furthermore, the computer program product that enables a computer system or data processing equipment device to act in pre-selected ways may be provided in a number of forms, including, but not limited to, original source code, assembly code, object code, machine language, encrypted or compressed versions of the foregoing and any and all equivalents.

In one embodiment, a computer program product is provided for indicating a likelihood of lung cancer, including squamous cell lung cancer (e.g. non-small cell lung squamous cell lung cancer or non-small cell lung large cell undifferentiated lung cancer), non-small cell non-adenocarcinoma lung cancer, non-small cell lung cancer, large cell lung cancer, small cell lung cancer and/or adenocarcinoma lung cancer. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers in the biological sample selected from the group of biomarkers provided in Table 1 or the mi-RNAs identified in Table 2; and code that executes a classification method that indicates an adenocarcinoma status of the individual as a function of the biomarker values.

In yet another embodiment, a computer program product is provided for indicating a likelihood of lung cancer, including squamous cell lung cancer (e.g. non-small cell lung squamous cell lung cancer or non-small cell lung large cell undifferentiated lung cancer), non-small cell non-adenocarcinoma lung cancer, non-small cell lung cancer, large cell lung cancer, small cell lung cancer and/or adenocarcinoma lung cancer. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers provided in Table 1 or the mi-RNAs set forth in Table 2; and code that executes a classification method that indicates an adenocarcinoma status of the individual as a function of the biomarker value.

The kit (i.e. diagnostic kit) can include reagents for determining, from a plasma sample of a subject, the amount of miRNAs or mutations in a gene based on assaying the nucleic acids, proteins, peptides or other biological molecule isolated from a lung cancer, including squamous cell lung cancer (e.g. non-small cell lung squamous cell lung cancer or non-small cell lung large cell undifferentiated lung cancer), non-small cell non-adenocarcinoma lung cancer, non-small cell lung cancer, large cell lung cancer, small cell lung cancer and/or adenocarcinoma lung cancer a circulating cell or the remnants of a circulating cell present in plasma, including a protein, peptide or other biological molecule. The nucleic acid can be a deoxyribonucleic acid (DNA), a ribonucleic acid (RNA) and/or an artificial nucleic acid, including an artificial nucleic acid analogue. Along with miRNAs, other RNAs include non-coding RNA (ncRNA), transfer RNA (tRNA), messenger RNA (mRNA), small interfering RNA (siRNA), piwi RNA (piRNA), small nuclear RNA (snoRNA), small nuclear (snRNA), extracellular RNA (exRNA), and ribosomal RNA (rRNA).

The disclosed methods and assays provide for convenient, efficient, and potentially cost-effective means to obtain data and information useful in assessing appropriate or effective therapies for treating patients. The kit can use conventional methods for detecting the biomarkers, whether a protein, peptide, other biological molecule or an RNA or a DNA to be assessed include protocols that examine the presence and/or expression of a desired nucleic acid, for example a SNP, in a sample. Tissue or cell samples from mammals can be conveniently assayed for, e.g., genetic-marker RNA, including in an embodiment an miRNA or DNAs using Northern, dot-blot, or polymerase chain reaction (PCR) analysis, array hybridization, RNase protection assay, or using DNA SNP chip microarrays, which are commercially available, including DNA micro array snapshots. For example, real-time PCR (RT-PCR) assays such as quantitative PCR assays are well known in the art.

Probes used for PCR can be labeled with a detectable marker, such as, for example, a radioisotope, fluorescent compound, bioluminescent compound, a chemiluminescent compound, metal chelator, or enzyme. Such probes and primers can be used to detect the presence of a mutation in a DNA, an RNA and in one embodiment, an miRNA in a sample and as a means for detecting a cell expressing the miRNA. As will be understood by the skilled artisan, a great many different primers and probes can be prepared based on known sequences and used effectively to amplify, clone, and/or determine the presence and/or levels of miRNAs.

Other DNA tests to determine whether a mutation exists include fluorescence in situ hybridization (FISH). Through the use of FISH, a mutation can be detected in cells, tissues, including lung tissue, including tumors, and further including lung tumors.

Protein or peptide identification can occur through the use of western blotting using techniques known in the art.

Other methods include protocols that examine or detect a mutation in a DNA or an RNA. These other methods include protocols that examine or detect miRNAs in a tissue or cell sample by microarray technologies. Using nucleic acid microarrays, test and control RNAs, including in an embodiment, miRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states can be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment.

The biomarkers are particularly useful in cancer diagnosis as their expression patterns is different when comparing healthy subjects with subjects that have lung adenocarcinoma. The expression of biomarkers typically includes both up- and down-regulated levels of miRNAs.

Additional biomarkers are set forth below in Table 1 for other forms of cancer. In an embodiment, the biomarkers set forth herein can determine if a patient has lung cancer or does not have lung cancer. In an embodiment, each is a form of lung cancer. In another embodiment, the cancer, and in an embodiment, lung cancer is squamous cell lung cancer (e.g. non-small cell lung squamous cell lung cancer or non-small cell lung large cell undifferentiated lung cancer), non-small cell non-adenocarcinoma lung cancer, non-small cell lung cancer, large cell lung cancer, small cell lung cancer and adenocarcinoma lung cancer.

The biomarkers below can be detected in DNA, including in an embodiment, one or mutations associated with a region of a gene, a snp or one or mutation on one or more chromosomes. The biomarkers below can also be detected in an RNA, including in an embodiment, an miRNA, a tRNA, an mRNA or other form of RNA.

TABLE 1 mRNA biomarkers and Proteins

| | Probe I.D. | Original RNA Name | Gene Name | Protein |
|---|---|---|---|---|
| 1 | 212121_at | Protein BE962354 tectonic family member 3 TCTN3 | TCTN3 | Tectonic-3 |
| 2 | 221081_s_at | DENN Domain Containing 2A | DENND1A | DENN domain-containing protein 1A |
| 3 | 209189_at | v-fos FBJ murine osteosarcoma viral oncogene homolog (associated with FOS gene) | FOS | Proto-oncogene c-Fos |
| 4 | 221192_x_at | MFSD11 Major Facilitator Superfamily Domain Containing 11 | MFSD11 | UNC93-like protein MFSD11 |
| 5 | 208447_s_at | Phosphoribosyl Pyrophosphate Synthetase 1 | PRPS1L1 | Ribose-phosphate pyrophosphokinase 3 |
| 6 | 203305_at | Coagulation Factor XIII A Chain | F13A1 | Coagulation factor XIII A chain |
| 7 | 206551_x_at | Kelch Like Family Member 24 | KLHL24 | Kelch-like protein 24 |
| 8 | 200957_s_at | Structure Specific Recognition Protein 1 | SSRP1 | FACT complex subunit SSRP1 |
| 9 | 200702_s_at | DEADH (Asp-Glu-Ala-AspHis) box polypeptide 24 | DDX24 | ATP-dependent RNA helicase DDX24 |
| 10 | 209234_at | kinesin family member 1B (KIF1B) | KIF1B | Kinesin-like protein KIF1B |
| 11 | 202938_x_at | CGI-96 protein (CGI-96) | RRP7A | Ribosomal RNA-processing protein 7 homolog A |
| 12 | 55081_at | MICAL-like 1 (MICALL1) | MICALL1 | MICAL-like protein 1 |
| 13 | 222166_at | chromosome 9 open reading frame 16 (C9orf16) | C9orf16 | UPF0184 protein C9orf16 |
| 14 | 208939_at | Selenium donor protein SPS | SEPHS1 | Selenide, water dikinase 1 |
| 15 | 206992_s_at | DMAC2L Distal Membrane Arm Assembly Complex 2 Like | DMAC2L | ATP synthase subunit s, mitochondrial |
| 16 | 206493_at | alpha 2b (platelet glycoprotein IIb of IIbIIIa complex (CD41B antigen) | ITGA2B | Integrin alpha-IIb |
| 17 | 204021_s_at | purine-rich element binding protein A (PURA) | PURA | Transcriptional activator protein Pur-alpha |
| 18 | 203228_at | platelet-activating factor acetylhydrolase, isoform Ib, gamma subunit (29kD) | PAFAH1B3 | Platelet-activating factor acetylhydrolase IB subunit gamma |
| 19 | 202671_s_at | Pyridoxal Kinase | PDXK | Pyridoxal kinase |
| 20 | 201895_at | v-raf murine sarcoma 3611 viral oncogene homolog1 | ARAF | Serine/threonine-protein kinase A-Raf |
| 21 | 201759_at | tubulin-specific chaperone d | TBCD | Tubulin-specific chaperone D |
| 22 | 1294_at | ubiquitin-activating enzyme E1 related protein mRNA | UBA1 | Ubiquitin-like modifier-activating enzyme 1 |

TABLE 1-continued mRNA biomarkers and Proteins

| | Probe I.D. | Original RNA Name | Gene Name | Protein |
|---|---|---|---|---|
| 23 | 209572_s_at | embryonic ectoderm development protein mRNA | EED | Polycomb protein EED |
| 24 | 204629_at | CGI-56 protein (CGI-56) | PARVB | Beta-parvin |
| 25 | 201485_s_at | reticulocalbin 2, EF-hand calcium binding domain | RCN2 | Reticulocalbin-2 |
| 26 | 55616_at | post-GPI attachment to proteins 3 (PGAP3) | PGAP3 | Post-GPI attachment to proteins factor 3 |
| 27 | 51200_at | chromosome 19 open reading frame 60 (C19orf60) | REX1BD aka 619orf60 | Required for excision 1-B domain-containing protein |
| 28 | 51176_at | mediator complex subunit 27 MED27 | MED27 | Mediator of RNA polymerase II transcription subunit 27 |
| 29 | 221756_at | phosphoinositide-3-kinase interacting protein 1 (PIK3IP1) | PIK3IP1 | Phosphoinositide-3-kinase-interacting protein 1 |
| 30 | 221749_at | YTH domain family, member 3 (YTHDF3) | YTHDF3 | YTH domain-containing family protein 3 |
| 31 | 219902_at | betaine-homocysteine methyltransferase 2 | BHMT2 | S-methylmethionine--homocysteine S-methyltransferase BHMT2 |
| 32 | 203427_at | DKFZP547E2110 protein | ASF1A | Histone chaperone ASF1A |
| 33 | 203074_at | annexin A8 (ANXA8), mRNA | ANXA8 | Annexin A8 |
| 34 | 201931_at | electron transfer flavoprotein, alphapolypeptide | ETFA | Electron transfer flavoprotein subunit alpha, mitochondrial |
| 35 | 201158_at | N-myristoyltransferase 1 | NMT1 | Glycylpeptide N-tetradecanoyltransferase 1 |
| 36 | 1438_at | HEK2 mRNA for protein tyrosine kinase receptor | EPHB3 | Ephrin type-B receptor 3 |
| 37 | 203390_s_at | kinesin family member 3C (KIF3C) | KIF3C | Kinesin-like protein KIF3C |
| 38 | 210102_at | similar to loss of heterozygosity, 11, chromosomal region 2, gene A (similar to VWA5A gene) | LOH11CR2A aka VWA5A | Loss of heterozygosity, 11, chromosomal region 2, gene A, isoform CRA_b |
| 39 | 218417_s_at | Solute Carrier Family 48 Member 1 | SLC48A1 | Heme transporter HRG1 |
| 40 | 64432_at | MAPKAPK5 antisense RNA 1 | MAPKAPK5-AS1 | Putative uncharacterized protein encoded by MAPKAPK5-AS1 |
| 41 | 60528_at | phospholipase A2, group IVB | PLA2G4B | Cytosolic phospholipase A2 beta |
| 42 | 57715_at | calcium homeostasis modulator 2 (CALHM2) | CALHM2 | Calcium homeostasis modulator protein 2 |
| 43 | 57703_at | SUMO1/sentrin specific peptidase 5 (SENP5) | SENP5 | Sentrin-specific protease 5 |
| 44 | 56256_at | SID1 transmembrane family, member 2 (SIDT2) | SIDT2 | SID1 transmembrane family member 2 |
| 45 | 55705_at | R3H domain containing 4(R3HDM4) | R3HDM4 | R3H domain-containing protein 4 |
| 46 | 55065_at | microtubule affinity-regulating kinase 4 (MARK4) | MARK4 | MAP/microtubule affinity-regulating kinase 4 |
| 47 | 51226_at | N53536 (unknown, possibly Riken cDNA) | | may be related to CYSRT1 gene |
| 48 | 51192_at | slingshot protein phosphatase 3 (SSH3) | SSH3 | Protein phosphatase Slingshot homolog 3 |
| 49 | 336_at | atonal homolog 1 (*Drosophila*) (ATOH1) | ATOH1 | Protein atonal homolog 1 |
| 50 | 222696_at | axin 2 (conductin, axil) | AXIN2 | Axin-2 |
| 51 | 222194_at | cDNA DKFZp547D096 | unknown | unknown |
| 52 | 221395_at | taste receptor, family B, member 3 | TAS2R13 | Taste receptor type 2 member 13 |
| 53 | 221393_at | G protein-coupled receptor 57 | unknown | unknown |

TABLE 1-continued

| | Probe I.D. | Original RNA Name | Gene Name | Protein |
|---|---|---|---|---|
| 54 | 221303_at | protocadherin beta 1 | PCDHB1 | Protocadherin beta-1 |
| 55 | 221301_at | NG37 protein | VWA7 | von Willebrand factor A domain-containing protein 7 |
| 56 | 221154_at | ring finger protein 18 | TRIM49 | Tripartite motif-containing protein 49 |
| 57 | 220323_at | cyclin N-terminal domain containing 2 (CNTD2) | CNTD2 | Cyclin N-terminal domain-containing protein 2 |
| 58 | 220213_at | hypothetical protein OVC10-2 | TSHZ2 | Teashirt homolog 2 |
| 59 | 220082_at | hypothetical protein FLJ20251 | | hypothetical protein FLJ20251 |
| 60 | 220074_at | cadherin-related family member 5 (CDHR5) | CDHR5 | Cadherin-related family member 5 |
| 61 | 220064_at | hypothetical protein FLJ11457 | | hypothetical protein FLJ11457 |
| 62 | 220002_at | kinesin family member 26B KIF26B | KIF26B | Kinesin-like protein KIF26B |
| 63 | 220001_at | peptidyl arginine deiminase, type V | PADI4 | Protein-arginine deiminase type-4 |
| 64 | 219736_at | zinc-binding protein Rbcc728 | TRIM36 | E3 ubiquitin-protein ligase TRIM36 |
| 65 | 219699_at | leucine-rich repeat LGI family, member 2 (LGI2) | LGI2 | Leucine-rich repeat LGI family member 2 |
| 66 | 219287_at | potassium large conductance calcium-activatedchannel, subfamily M, beta member 4 | KCNMB4 | Calcium-activated potassium channel subunit beta-4 |
| 67 | 207063_at | hypothetical protein PRO2834 | TTTY14 | no translational proteins found |
| 68 | 206338_at | Hu antigen C | ELAVL3 | ELAV-like protein 3 |
| 69 | 205564_at | JM27 protein | PAGE4 | P antigen family member 4 |
| 70 | 205251_at | (PER2), transcript variant 1, mRNA | PER2 | Period circadian protein homolog 2 |
| 71 | 204474_at | zinc finger protein 142 (clone pHZ-49) (ZNF142) | ZNF142 | Zinc finger protein 142 (Clone pHZ-49), isoform CRA_b |
| 72 | 203547_at | U47924 CD4 molecule CD4 920 | CD4 | U47924 CD4 molecule (may not be protein but may be an antigen) |
| 73 | 203522_at | copper chaperone for superoxide dismutase | CCS | Copper chaperone for superoxide dismutase |
| 74 | 203413_at | nel (chicken)-like 2 (NELL2) | NELL2 | Protein kinase C-binding protein NELL2 |
| 75 | 203286_at | KIAA1100 protein | RNF44 | RING finger protein 44 |
| 76 | 203068_at | kelch-like family member 21 KLHL21 | KLHL21 | Kelch-like protein 21 |
| 77 | 202865_at | (Hsp40) homolog, subfamily B, member 12 | DNAJB12 | DnaJ homolog subfamily B member 12 |
| 78 | 201725_at | D123 gene product | CDC123 | Cell division cycle protein 123 homolog |
| 79 | 201181_at | guanine nucleotide binding protein (G protein), alpha inhibiting activity polypeptide 3 | GNAI3 | Guanine nucleotide-binding protein G(i) subunit alpha |
| 80 | 1729_at | TNF receptor-1 associated protein (TRADD) mRNA | TRADD | Tumor necrosis factor receptor type 1-associated DEATH domain protein |
| 81 | 1316_at | thyroid hormone receptor, alpha (THRA) | THRA | Thyroid hormone receptor alpha |

_at = all the probes hit one known transcript;
_a = all probes in the set hit alternate transcripts from the same gene;
_s = all probes in the set hit transcripts from different genes;
_x = some probes hit transcripts from different genes.

Other methods for determining the level of the biomarker besides RT-PCR or another PCR-based method include proteomics techniques, as well as individualized genetic profiles. Individualized genetic profiles can be used in the diagnosis, prognosis and/or therapy of lung cancer based on patient response at a molecular level. The specialized microarrays herein, (e.g., oligonucleotide microarrays or cDNA microarrays) can include one or more biomarkers having expression profiles that correlate with either sensitivity or resistance to one or more antibodies.

The one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126 and/or 127 biomarkers can be stored in a liquid or in a dry form, including, following lyophilization. If the one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126 and/or 127 biomarkers are stored dry, the one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123. 124, 125, 126 and/or 127 biomarkers can be resuspended using water or a solution one of skill in the art would know would know would result in the stable resuspension of the one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124. 125, 126 and/or 127 biomarkers.

miRNA as Biomarkers

Table 2 includes a list of miRNA biomarkers.

TABLE 2

| | miRNA's as Biomarkers |
|---|---|
| | miRNA |
| 1 | hsa-miR-1204 |
| 2 | hsa-miR-141-3p |
| 3 | hsa-miR-1827 |
| 4 | hsa-miR-938 |
| 5 | hsa-miR-125b-5p |
| 6 | hsa-miR-297 |
| 7 | hsa-miR-10a-5p |
| 8 | hsa-miR-145-5p |

TABLE 2-continued

| | miRNA's as Biomarkers |
|---|---|
| | miRNA |
| 9 | hsa-miR-217 |
| 10 | hsa-miR-3185 |
| 11 | hsa-miR-21-5p |
| 12 | hsa-miR-363-3p |
| 13 | hsa-miR-631 |
| 14 | hsa-miR-655 |
| 15 | hsa-miR-1245b-5p |
| 16 | hsa-miR-369-3p |
| 17 | hsa-miR-875-3p |
| 18 | hsa-miR-105-5p |
| 19 | hsa-miR-1253 |
| 20 | hsa-miR-1285-3p |
| 21 | hsa-miR-512-5p |
| 22 | hsa-miR-550b-3p |
| 23 | hsa-miR-571 |
| 24 | hsa-miR-935 |
| 25 | hsa-miR-145-5p |
| 26 | hsa-miR-3185 |
| 27 | hsa-miR-1285-3p |
| 28 | hsa-miR-125b-5p |
| 29 | hsa-miR-550b-3p |

Method of Diagnoses Using miRNAs as Biomarkers

One or more of the biomarkers can be used in a method of diagnosing cancer or determining a prognosis of a test subject with cancer. In this manner, one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126 and/or 127 biomarkers can be used in a method of diagnosing cancer or determining a prognosis of a test subject with cancer. In this manner, at least one biomarker or a combination of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124. 125, 126 and/or 127 biomarkers can be used in a method of diagnosing cancer or determining a prognosis of a test subject with cancer.

In this manner, no more than one biomarker or a combination of no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126 and/or 127 biomarkers can be used in a method of diagnosing cancer or determining a prognosis of a test subject with cancer. In this manner, about one biomarker or a combination of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126 and/or 127 biomarkers can be used in a method of diagnosing cancer or determining a prognosis of a test subject with cancer.

In a first step, the expression levels of one or more miRNAs are measured in plasma samples from subjects with cancer. In an embodiment, the expression levels of one biomarker or a combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124. 125, 126 and/or 127 biomarkers can be used to generate a footprint or signature for subsequent diagnosis of patients. In an embodiment, the expression levels of at least one biomarker or a combination of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126 and/or 127 biomarkers can be used to generate a footprint or signature for subsequent diagnosis of patients.

In an embodiment, the expression levels of no more than one biomarker or a combination of no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126 and/or 127 biomarkers can be used to generate a footprint or signature for subsequent diagnosis of patients. In an embodiment, the expression levels of about one biomarker or a combination of about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123. 124, 125, 126 and/or 127 biomarkers can be used to generate a footprint or signature for subsequent diagnosis of patients.

Next, expression levels of the same nucleic acids, including DNA and/or RNA and further including miRNAs are measured in plasma, blood or tissue samples from healthy subjects. This is used as a control. Thereafter, samples from healthy patients can be compared to identifying miRNAs that have altered levels of expression in the plasma samples from the subjects with cancer. A biomarker fingerprint or signature can be created from the miRNAs with altered levels of expression. This can be used for diagnosing or determining the prognosis of cancer in the test subject by comparing of levels of miRNAs from plasma of the test subject. Conventional statistical analysis can be used to determine, for example, confidence levels.

FIG. 1 depicts a method of combining results from biomarkers to achieve a final categorical determination. Multiple biomarkers can be measured in a patient. The results can be compiled to produce a single categorical determination according to the following steps.

1. For a patient or sample, on which was measured a set of biomarkers (each biomarker is $b_i$ where i is at least 1).
2. Optionally transform each biomarker using a mathematical or logical operation.
3. For a subset of the i biomarkers with j biomarkers in the subset (at least 2 member biomarkers per set), optionally integrate the biomarker measures using a mathematical or logical operation (e.g. $b_1/b_2$) to form an "integrated biomarker".
4. Optionally perform step 3 on k subsets.
5. Optionally iterate original biomarkers and integrated biomarkers through steps 2, 3, 4 to result in a final, continuous score.
6. Apply t thresholds (where t is 1 or greater) to categorize the patient or sample into a decision category (diagnostic, prognostic, treatment responder, etc.)

An alternative approach includes the following steps.
1. For a patient or sample, on which was measured a set of biomarkers (each biomarker is $b_i$ where i is at least 1).
2. Mathematically transform each biomarker (the definition of transform may be no transform, e.g. no mathematical operation or a non-modifying operation such as multiplying by 1).
3. Optionally mathematically integrate from 2 to i of the biomarkers into a final score (e.g. by weights applied to each and results added, like linear regression, or by other algorithmic steps including iterative steps).
4. Using t thresholds (where t is at least 1), categorize the patient or sample into 1 of t+1 categories.

Diagnostic Categories of Biomarkers

Applicants have discovered that particular biomarkers are effective in distinguishing among categories of lung cancer. Embodiments include a system and method of distinguishing between lung cancers, including (SCLC, NSCLC, NSCLC adenocarcinoma, NSCLC squamous carcinoma and NSCLC large cell undifferentiated). The categories and corresponding biomarkers are listed in Table 3. Several biomarkers can be used in multiple categories as shown in Table 4.

TABLE 3

Diagnostic Categories of Biomarkers

| No. | Gene I.D. | Gene Name | Category |
|---|---|---|---|
| 22 | 1294 | UBA1 | squamous |
| 20 | 201895 | ARAF | squamous |
| 77 | 202865 | DNAJB12 | squamous |
| 76 | 203068 | KLHL21 | squamous |
| 33 | 203074 | ANXA8 | squamous |
| 73 | 203522 | CCS | squamous |
| 71 | 204474 | ZNF142 | squamous |
| 70 | 205251 | PER2 | squamous |
| 68 | 206338 | ELAVL3 | squamous |
| 63 | 220001 | PADI4 | squamous |
| 56 | 221154 | TRIM49 | squamous |
| 30 | 221749 | YTHDF3 | squamous |

TABLE 3-continued

Diagnostic Categories of Biomarkers

| No. | Gene I.D. | Gene Name | Category |
|---|---|---|---|
| 29 | 221756 | PIK3IP1 | squamous |
| 13 | 222166 | C9orf16 | squamous |
| 50 | 222696 | AXIN2 | squamous |
| 28 | 51176 | MED27 | squamous |
| 27 | 51200 | REX1BD aka 619orf60 | squamous |
| 46 | 55065 | MARK4 | Squamous |
| 26 | 55616 | PGAP3 | squamous |
| 40 | 64432 | MAPKAPK5-AS1 | squamous |
| 22 | 1294 | UBA1 | SCLC |
| 81 | 1316 | THRA | SCLC |
| 36 | 1438 | EPHB3 | SCLC |
| 35 | 201158 | NMT1 | SCLC |
| 18 | 203228 | PAFAH1B3 | SCLC |
| 75 | 203286 | RNF44 | SCLC |
| 32 | 203427 | ASF1A | SCLC |
| 31 | 219902 | BHMT2 | SCLC |
| 53 | 221393 | Unknown (G protein-coupled receptor 57) | SCLC |
| 30 | 221749 | YTHDF3 | SCLC |
| 13 | 222166 | C9orf16 | SCLC |
| 51 | 222194 | Unknown (cDNA DKFZp547D096) | SCLC |
| 27 | 51200 | REX1BD aka 619orf60 | SCLC |
| 47 | 51226 | N53536 (unknown, possibly Riken cDNA) | SCLC |
| 12 | 55081 | MICALL1 | SCLC |
| 42 | 57715 | CALHM2 | SCLC |
| 22 | 1294 | UBA1 | NSCLC |
| 36 | 1438 | EPHB3 | NSCLC |
| 78 | 201725 | CDC123 | NSCLC |
| 34 | 201931 | ETFA | NSCLC |
| 18 | 203228 | PAFAH1B3 | NSCLC |
| 32 | 203427 | ASF1A | NSCLC |
| 65 | 219699 | LGI2 | NSCLC |
| 58 | 220213 | TSHZ2 | NSCLC |
| 54 | 221303 | PCDHB1 | NSCLC |
| 52 | 221395 | TAS2R13 | NSCLC |
| 12 | 55081 | MICALL1 | NSCLC |
| 45 | 55705 | R3HDM4 | NSCLC |
| 9 | 200702 | DDX24 | lung, no lung |
| 8 | 200957 | SSRP1 | lung, no lung |
| 25 | 201485 | RCN2 | lung, no lung |
| 21 | 201759 | TBCD | lung, no lung |
| 19 | 202671 | PDXK | lung, no lung |
| 11 | 202938 | RRP7A | lung, no lung |
| 6 | 203305 | F13A1 | lung, no lung |
| 37 | 203390 | KIF3C | lung, no lung |
| 17 | 204021 | PURA | lung, no lung |
| 24 | 204629 | PARVB | lung, no lung |
| 16 | 206493 | ITGA2B | lung, no lung |
| 7 | 206551 | KLHL24 | lung, no lung |
| 15 | 206992 | DMAC2L | lung, no lung |
| 5 | 208447 | PRPS1L1 | lung, no lung |
| 14 | 208939 | SEPHS1 | lung, no lung |
| 3 | 209189 | FOS | lung, no lung |
| 10 | 209234 | KIF1B | lung, no lung |
| 23 | 209572 | EED | lung, no lung |
| 38 | 210102 | LOH11CR2A aka VWA5A | lung, no lung |
| 1 | 212121 | TCTN3 | lung, no lung |
| 39 | 218417 | SLC48A1 | lung, no lung |
| 2 | 221081 | DENND1A | lung, no lung |
| 4 | 221192 | MFSD11 | lung, no lung |
| 29 | 201181 | PIK3IP1 | lung, no lung |
| 20 | 201895 | ARAF | large cell |
| 34 | 201931 | ETFA | large cell |
| 72 | 203547 | CD4 | large cell |
| 69 | 205564 | PAGE4 | large cell |
| 67 | 207063 | TTTY14 | large cell |
| 66 | 219287 | KCNMB4 | large cell |
| 62 | 220002 | KIF26B | large cell |
| 61 | 220064 | Unknown (hypothetical protein FLJ11457) | large cell |
| 60 | 220074 | CDHR5 | large cell |
| 57 | 220323 | CNTD2 | large cell |
| 55 | 221301 | VWA7 | large cell |
| 49 | 336 | ATOH1 | large cell |
| 48 | 51192 | SSH3 | large cell |
| 44 | 56256 | SIDT2 | large cell |
| 80 | 1729 | TRADD | adenocarcinoma |
| 35 | 201158 | NMT1 | adenocarcinoma |
| 20 | 201895 | ARAF | adenocarcinoma |
| 33 | 203074 | ANXA8 | adenocarcinoma |
| 18 | 203228 | PAFAH1B3 | adenocarcinoma |
| 74 | 203413 | NELL2 | adenocarcinoma |
| 64 | 219736 | TRIM36 | adenocarcinoma |
| 31 | 219902 | BHMT2 | adenocarcinoma |
| 59 | 220082 | Unknown (hypothetical protein FLJ20251) | adenocarcinoma |
| 29 | 221756 | PIK3IP1 | adenocarcinoma |
| 13 | 222166 | C9orf16 | adenocarcinoma |
| 28 | 51176 | MED27 | adenocarcinoma |
| 12 | 55081 | MICALL1 | adenocarcinoma |
| 26 | 55616 | PGAP3 | adenocarcinoma |
| 43 | 57703 | SENP5 | adenocarcinoma |
| 41 | 60528 | PLA2G4B | adenocarcinoma |

TABLE 4

Biomarkers with Multiple Categories

| No. | Gene I.D. | | Category |
|---|---|---|---|
| 22 | 1294 | UBA1 | Squamous, NSCLC, SCLC |
| 36 | 1438 | EPHB3 | NSCLC, SCLC |
| 35 | 201158 | NMT1 | Adeno, SCLC |
| 20 | 201895 | ARAF | Squamous, Adeno, Large-cell |
| 34 | 201931 | ETFA | Large-cell, NSCLC |
| 33 | 203074 | ANXA8 | Squamous, Adeno |
| 18 | 203228 | PAFAH1B3 | Adeno, NSCLC, SCLC |
| 32 | 203427 | ASF1A | NSCLC, SCLC |
| 31 | 219902 | BHMT2 | Adeno, SCLC |
| 30 | 221749 | YTHDF3 | Squamous, SCLC |
| 29 | 221756 | PIK3IP1 | Squamous, Adeno |
| 13 | 222166 | C9orf16 | Squamous, Adeno, SCLC |
| 28 | 51176 | MED27 | Squamous, Adeno |
| 27 | 51200 | REX1BD aka 619orf60 | Squamous, SCLC |
| 12 | 55081 | MICALL1 | Adeno, NSCLC, SCLC |
| 26 | 55616 | PGAP3 | Squamous, Adeno |

Diagnostic Kit for Rapid Screening of Lung Cancer

The following working example is based on configurations described above. Embodiments of the invention can be compiled into a diagnostic kit for diagnosing lung adenocarcinoma. The kit can identify one or more target cells that have the biomarkers for lung cancer in plasma from a test subject.

The kit can include a collection of nucleic acid molecules such that each nucleic acid molecule encodes a miRNA sequence. The nucleic acid molecules can be used to identify variations in expression levels of one or more miRNAs in a plasma sample from a test subject. The expression levels of the miRNAs can be used in a comparison/analysis of test samples with a fingerprint indicative of the presence of cancer.

In certain embodiments, the present disclosure provides kits for diagnosing lung cancer. In one embodiment, the lung cancer is an adenocarcinoma. The kits can include one biomarker or a combination of 2, 3, 4, 5, 6, 7, 8, 9, 10, 11, 12, 13, 14, 15, 16, 17, 18, 19, 20, 21, 22, 23 and/or 24 biomarkers disclosed herein. The skilled artisan will appreciate that the number of biomarkers may be varied without departing from the nature of the present disclosure, and thus other combinations of biomarkers are also encompassed by the present disclosure. The skilled artisan will know which one biomarker or a combination of 2, 3, 4, 5, 6, 7, 8, 9, 10, 11, 12, 13, 14, 15, 16, 17, 18, 19, 20, 21, 22, 23 and/or 24 biomarkers to use based on the symptoms of the patient suffering from lung cancer.

In a specific embodiment, a kit includes the one biomarker or a combination of 2, 3, 4, 5, 6, 7, 8, 9, 10, 11, 12, 13, 14, 15, 16, 17, 18, 19, 20, 21, 22, 23 and/or 24 biomarkers disclosed herein. In certain embodiments, the kit is for diagnosing lung cancer. In another embodiment, the kit is for diagnosing an adenocarcinoma. The kit can further optionally include instructions for use. The kit can further optionally include (e.g., comprise, consist essentially of, consist of) tubes, applicators, vials or other storage container with the above mentioned biomarker and/or vials containing one or more of the biomarkers. In an embodiment, each biomarker is in its own tube, applicator, vial or storage container or 2, 3, 4, 5, 6, 7, 8, 9, 10, 11, 12, 13, 14, 15, 16, 17, 18, 19, 20, 21, 22, 23 and/or 24 biomarkers are in a tube, applicator, vial or storage container.

The kits, regardless of type, will generally include one or more containers into which the one biomarker or a combination of 2, 3, 4, 5, 6, 7, 8, 9, 10, 11, 12, 13, 14, 15, 16, 17, 18, 19, 20, 21, 22, 23 and/or 24 biomarkers are placed and, preferably, suitably aliquoted. The components of the kits may be packaged either in aqueous media or in lyophilized form.

EXAMPLES

The following non-limiting examples are provided for illustrative purposes only in order to facilitate a more complete understanding of representative embodiments now contemplated. These examples are intended to be a mere subset of all possible contexts in which the components of the formulation may be combined. Thus, these examples should not be construed to limit any of the embodiments described in the present specification, including those pertaining to the type and amounts of components of the formulation and/or methods and uses thereof.

Example 1

Diagnosing Lung Cancer Using miRNA Biomarkers

A male smoker aged 56 presents to his health care provider with a recurring cough and occasional blood in the sputum. The provider draws a sample of blood and sends it to a lab to test for lung cancer. The blood sample is prepared and the plasma is obtained. The plasma is then tested to identify the presence of biomarkers associated with lung cancer. The lab uses one or more of the following biomarkers in its test: hsa-miR-1204, hsa-miR-141-3p, hsa-miR-1827, hsa-miR-938, hsa-miR-125b-5p, hsa-miR-297, hsa-miR-10a-5p, hsa-miR-145-5p, hsa-miR-217, hsa-miR-3185, hsa-miR-21-5p, hsa-miR-363-3p, hsa-miR-631, hsa-miR-655, hsa-miR-1245b-5p, hsa-miR-369-3p, hsa-miR-875-3p, hsa-miR-105-5p, hsa-miR-1253, hsa-miR-1285-3p, hsa-miR-512-5p, hsa-miR-550b-3p, hsa-miR-571, hsa-miR-935, hsa-miR-145-5p, hsa-miR-3185, hsa-miR-1285-3p, hsa-miR-125b-5p and hsa-miR-550b-3p. Common hybridization based assays are used to determine the levels of each biomarkers in the patient sample.

Based on the test results, the healthcare provider determines that the one or more biomarkers used to test for lung cancer, and more directly, an adenocarcinoma are indicative of its presence. The patient is informed that he has lung cancer, and more specifically, an adenocarcinoma. A chest x-ray can help determine the location and extent of cancer.

The biomarkers can identify the cancer in its early stages when more treatment options are available. Based on these results, the patient is referred to specialist for further evaluation and treatment.

Example 2

Diagnosing Lung Cancer Using mRNA Biomarkers

In this example, a patient wishes to be screened for lung cancer. The biomarkers can accurately identify the cancer in its early stages. Further, the use of biomarkers is less invasive than conventional methods (i.e. chest x-way and biopsy). A health care provider draws a sample of blood from the patient. Thereafter, the levels of mRNA biomarkers can be determined in the blood, plasma, serum or a derivative of the blood.

The lab uses two or more of the following biomarkers in its test (identified by gene): DDX24, SSRP1, RCN2, TBCD, PDXK, RRP7A, F13A1, KIF3C, PURA, PARVB, ITGA2B, KLHL24, DMAC2L, PRPS1L1, SEPHS1, FOS, KIF1B, EED, LOH11CR2A (aka VWA5A), TCTN3, SLC48A1, DENND1A, MFSD11 and PIK3IP. Common hybridization-based assays are used to determine the levels of each biomarker in the patient sample. The expression levels of the mRNAs are entered into a computer such as a laptop or a tablet computer. The computer compiles the expression levels to yield a score. The score is compared to one or more threshold values to diagnose or determine the prognosis of the lung cancer.

Based on the score, the healthcare provider determines that the patient has lung cancer. A chest x-ray can determine the location and extent of cancer. The patient is referred to specialist for further evaluation and treatment.

Example 3

Diagnosing Squamous Cell Lung Cancer Using mRNA Biomarkers

Squamous cell carcinoma is one type of non-small cell lung cancer. The others are adenocarcinoma and large cell carcinoma. In this example, a health care provide wishes to screen a patient for squamous cell lung cancer. The biomarkers can distinguish squamous cell carcinoma from other types of lung cancer (i.e. adenocarcinoma, large cell carcinoma and SCLC). Further, the use of biomarkers is less invasive than conventional methods (i.e. chest x-way and biopsy). A health care provider draws a sample of blood from the patient. Thereafter, the levels of mRNA biomarkers can be determined in the blood, plasma, serum or a derivative of the blood.

The lab uses two or more of the following biomarkers in its test (identified by gene): UBA1, ARAF, DNAJB12, KLHL21, ANXA8, CCS, ZNF142, PER2, ELAVL3, PADI4, TRIM49, YTHDF3, PIK3IP1, C9orf16, AXIN2, MED27, REX1BD aka 619orf60, MARK4, PGAP3, MAPKAPK5-AS1. Common hybridization-based assays are used to determine the levels of each biomarker in the patient sample. The expression levels of the mRNAs are entered into a computer such as a laptop or a tablet computer. The computer compiles the expression levels to yield a score. The score is compared to one or more threshold values to diagnose or determine the prognosis of the lung cancer.

Based on the score, the healthcare provider determines that the patient has squamous cell lung cancer. A chest x-ray can determine the location and extent of cancer. The patient is referred to specialist for further evaluation and treatment.

Example 4

Diagnosing Small Cell Lund Cancer (SCLC) Using Biomarkers

In this example, a patient suffers from lung cancer. Biomarkers are used to identify the category as Small Cell Lung Cancer (SCLC) in a patient. Further, the use of biomarkers is less invasive than conventional methods (i.e. chest x-way and biopsy). A health care provider draws a sample of blood from the patient. Thereafter, the levels of mRNA biomarkers can be determined in the blood, plasma, serum or a derivative of the blood.

The lab uses two or more of the following biomarkers in its test (identified by gene): UBA1, THRA, EPHB3, NMT1, PAFAH1B3, RNF44, ASF1A, BHMT2, YTHDF3, C9orf16, REX1BD (aka 619orf60), N53536, MICALL1, CALHM2. Common hybridization-based assays are used to determine the levels of each biomarker in the patient sample. The expression levels of the mRNAs are entered into a computer such as a laptop or a tablet computer. The computer compiles the expression levels to yield a score. The score is compared to one or more threshold values to diagnose or determine the prognosis of SCLC.

Based on the score, the healthcare provider determines that the patient has SCLC. Additional biomarkers can be analyzed to determine the type of SCLC. A chest x-ray can determine the location and extent of cancer. The patient is referred to specialist for further evaluation and treatment.

Example 5

Diagnosing Non-Small Cell Lung Cancer (NSCLC, not Adenocarcinoma) Using Biomarkers In this example, a patient suffers from lung cancer. Biomarkers are used to identify the category as Non-small Cell Lung Cancer (NSCLC) in a patient. Further, the use of biomarkers is less invasive than conventional methods (i.e. chest x-way and biopsy). A health care provider draws a sample of blood from the patient. Thereafter, the levels of mRNA biomarkers can be determined in the blood, plasma, serum or a derivative of the blood.

The lab uses two or more of the following biomarkers in its test (identified by gene): UBA1, EPHB3, CDC123, ETFA, PAFAH1B3, ASF1A, LGI2, TSHZ2, PCDHB1, TAS2R13, MICALL1 and R3HDM4. Common hybridization-based assays are used to determine the levels of each biomarker in the patient sample. The expression levels of the mRNAs are entered into a computer such as a laptop or a tablet computer. The computer compiles the expression levels to yield a score. The score is compared to one or more threshold values to diagnose or determine the prognosis of the NSCLC.

Based on the score, the healthcare provider determines that the patient has SCLC. A chest x-ray can determine the location and extent of cancer. The patient is referred to specialist for further evaluation and treatment.

Example 6

Diagnosing Large Cell Lung Cancer Using Biomarkers

In this example, a patient suffers from lung cancer. Biomarkers are used to identify the type as Large Cell Lung Cancer in a patient. The use of biomarkers is less invasive than conventional methods (i.e. chest x-way and biopsy). A health care provider draws a sample of blood from the patient. Thereafter, the levels of mRNA biomarkers can be determined in the blood, plasma, serum or a derivative of the blood.

The lab uses two or more of the following biomarkers in its test (identified by gene): ARAF, ETFA, CD4, PAGE4, TTTY14, KCNMB4, KIF26B, CDHR5, CNTD2, VWA7, ATOH1, SSH3 and SIDT2. Common hybridization-based assays are used to determine the levels of each biomarker in the patient sample. The expression levels of the mRNAs are entered into a computer such as a laptop or a tablet computer. The computer compiles the expression levels to yield a score. The score is compared to one or more threshold values to diagnose or determine the prognosis of the Large Cell Lung Cancer.

Based on the score, the healthcare provider determines that the patient has Large Cell Lung Cancer. A chest x-ray can determine the location and extent of cancer. The patient is referred to specialist for further evaluation and treatment.

Example 7

Diagnosing Adenocarcinoma Using Biomarkers

Adenocarcinoma is one type of NSCLC. In this example, a patient suffers from NSCLC. Biomarkers are used to identify the category as adenocarcinoma. The use of biomarkers is less invasive than conventional methods (i.e. chest x-way and biopsy). A health care provider draws a sample of blood from the patient. Thereafter, the levels of mRNA biomarkers can be determined in the blood, plasma, serum or a derivative of the blood.

The lab uses two or more of the following biomarkers in its test (identified by gene): TRADD, NMT1, ARAF, ANXA8, PAFAH1B3, NELL2, TRIM36, BHMT2, PIK3IP1, C9orf16, MED27, MICALL1, PGAP3, SENP5, PLA2G4B. Common hybridization-based assays are used to determine the levels of each biomarker in the patient sample. The expression levels of the mRNAs are entered into a computer such as a laptop or a tablet computer. The computer compiles the expression levels to yield a score. The score is compared to one or more threshold values to diagnose or determine the prognosis of the adenocarcinoma.

Based on the score, the healthcare provider determines that the patient has adenocarcinoma. A chest x-ray can determine the location and extent of cancer. The patient is referred to specialist for further evaluation and treatment.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

What is claimed is:

1. A method of diagnosing a lung cancer or determining a prognosis of a subject with a lung cancer, comprising the steps of:
   a) measuring the expression level of at least one nucleic acid in a test sample from the subject,
   b) receiving the expression level of the at least one nucleic acid in the test sample by a computer and
   c) comparing the expression level of the at least one nucleic acid in the test sample to a level in a base sample for the same at least one nucleic acid, protein or peptide, and
   d) receiving a result comparing the expression levels of the at least one nucleic acid in the test sample measured in a) and the base sample measured in c),
   e) diagnosing or determining the prognosis of lung cancer based on altered expression of the at least one nucleic acid in the test sample as compared to the base sample as determined in a computer, and
   f) treating the subject for lung cancer based on the diagnosis or prognosis,
   wherein the at least one nucleic acid is comprised of mRNA encoded by the genes DMAC2L and REX1BD.

2. The method of claim 1, wherein the lung cancer is squamous cell lung cancer, non-small cell lung cancer, large cell lung cancer, small cell lung cancer and/or adenocarcinoma lung cancer.

3. The method of claim 1, wherein the at least one nucleic acid is comprised of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 different nucleic acids.

4. The method of claim 1, wherein the at least one nucleic acid is comprised of no more than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81 different nucleic acids.

5. A method of diagnosing a lung cancer or determining a prognosis of a subject with a lung cancer, the method comprising the steps of:
   a) measuring expression levels of at least two nucleic acids in a test sample from the subject,
   b) receiving the expression levels with a computer,
   c) compiling the expression levels to yield a score, and
   d) comparing the score to one or more threshold values to diagnose or determine the prognosis of lung cancer, and
   e) treating the subject for lung cancer based on the diagnosis or prognosis,
   wherein the at least two nucleic acids is comprised of mRNA encoded by the genes DMAC2L and REX1BD.

6. The method of claim 5, wherein the lung cancer is squamous cell lung cancer, non-small cell lung cancer, large cell lung cancer, small cell lung cancer and/or adenocarcinoma lung cancer.

7. The method of claim 5, wherein the at least two nucleic acids is comprised of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81, different nucleic acids.

8. The method of claim 5, wherein the at least two nucleic acids is comprised of no more than 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, or 81, different nucleic acids.

9. The method of claim 1, wherein the at least one nucleic acid further comprises one or more mRNAs encoded by the genes TCTN3, DENND1A, FOS, MFSD11, PRPS1L1, F13A1, KLHL24, SSRP1, DDX24, KIF1B, RRP7A, MICALL1, C9orf16, SEPHS1, ITGA2B, PURA, PAFAH1B3, PDXK, ARAF, TBCD, UBA1, EED, PARVB, RCN2, PGAP3, MED27, PIK3IP1, YTHDF3, BHMT2, ASF1A, ANXA8, ETFA, NMT1, EPHB3, KIF3C, LOH11CR2A (aka VWASA), SLC48A1, MAPKAPK5-AS1, PLA2G4B, CALHM2, SENP5, SIDT2, R3HDM4, MARK4, SSH3, ATOH1, AXIN2, TAS2R13, PCDHB1, VWA7, TRIM49, CNTD2, TSHZ2, CDHR5, KIF26B, PADI4, TRIM36, LGI2, KCNMB4, TTTY14, ELAVL3, PAGE4, PER2, ZNF142, CD4, CCS, NELL2, RNF44, KLHL21, DNAJB12, CDC123, GNAI3, TRADD and THRA.

10. The method of claim 1, further comprising a step of measuring the expression level of at least one miRNA, the at least on miRNA selected from the group of hsa-miR-1204, hsa-miR-141-3p, hsa-miR-1827, hsa-miR-938, hsa-miR-125b-5p, hsa-miR-297, hsa-miR-10a-5p, hsa-miR-145-5p, hsa-miR-217, hsa-miR-3185, hsa-miR-21-5p, hsa-miR-363-3p, hsa-miR-631, hsa-miR-655, hsa-miR-1245b-5p, hsa-miR-369-3p, hsa-miR-875-3p, hsa-miR-105-5p, hsa-miR-1253, hsa-miR-1285-3p, hsa-miR-512-5p, hsa-miR-550b-3p, hsa-miR-571 and hsa-miR-935.

11. The method of claim 1, further comprising a step of measuring the expression level of at least one protein, the at least on protein selected from the group of Tectonic-3, DENN domain-containing protein 1A, Proto-oncogene c-Fos, UNC93-like protein MFSD11, Ribose-phosphate pyrophosphokinase 3, Coagulation factor XIII A chain, Kelch-like protein 24, FACT complex subunit SSRP1, ATP-dependent RNA helicase DDX24, Kinesin-like protein KIF1B, Ribosomal RNA-processing protein 7 homolog A, MICAL-like protein 1, UPF0184 protein C9orf16, Selenide, water dikinase 1, ATP synthase subunit s, mitochondrial, Integrin alpha-11b, Transcriptional activator protein Pur-alpha, Platelet-activating factor acetylhydrolase IB subunit gamma, Pyridoxal kinase, Serine/threonine-protein kinase A-Raf, Tubulin-specific chaperone D, Ubiquitin-like modifier-activating enzyme 1, Polycomb protein EED, Beta-parvin, Reticulocalbin-2, Post-GPI attachment to proteins factor 3, Required for excision 1-B domain-containing protein, Mediator of RNA polymerase II transcription subunit 27, Phosphoinositide-3-kinase-interacting protein 1, YTH domain-containing family protein 3, S-methylmethionine-homocysteine S-methyltransferase BHMT2, Histone chaperone ASF1A, Annexin A8, Electron transfer flavoprotein subunit alpha mitochondrial, Glycylpeptide N-tetradecanoyltransferase 1, Ephrin type-B receptor 3, Kinesin-like protein KIF3C, Loss of heterozygosity, 11, chromosomal region 2, gene A, isoform CRA_b, Heme transporter HRG1, Putative uncharacterized protein encoded by MAPKAPK5-AS1, Cytosolic phospholipase A2 beta, Calcium homeostasis modulator protein 2, Sentrin-specific protease 5, SID1 transmembrane family member 2, R3H domain-containing protein 4, MAP/microtubule affinity-regulating kinase 4, CYSRT1 gene, Protein phosphatase Slingshot homolog 3, Protein atonal homolog 1, Axin-2, Taste receptor type 2 member 13, Protocadherin beta-1, von Willebrand factor A domain-containing protein 7, Tripartite motif-containing protein 49, Cyclin N-terminal domain-containing protein 2, Teashirt homolog 2, hypothetical protein FLJ20251, Cadherin-related family member 5, hypothetical protein FLJ11457, Kinesin-like protein KIF26B, Protein-arginine deiminase type-4, E3 ubiquitin-protein ligase TRIM36, Leucine-rich repeat LGI family member 2, Calcium-activated potassium channel subunit beta-4, ELAV-like protein 3, P antigen family member 4, Period circadian protein homolog 2, Zinc finger protein 142 (Clone pHZ-49), isoform CRA_b, U47924 CD4 molecule, Copper chaperone for superoxide dismutase, Protein kinase C-binding protein NELL2, RING finger protein 44, Kelch-like protein 21, DnaJ homolog subfamily B member 12, Cell division cycle protein 123 homolog, Guanine nucleotide-binding protein G(i) subunit alpha, Tumor necrosis factor receptor type 1-associated DEATH domain protein and Thyroid hormone receptor alpha.

12. The method of claim 5, wherein the at least two nucleic acids further comprise one or more mRNAs encoded by the genes TCTN3, DENND1A, FOS, MFSD11, PRPS1L1, F13A1, KLHL24, SSRP1, DDX24, KIF1B, RRP7A, MICALL1, C9orf16, SEPHS1, ITGA2B, PURA, PAFAH1B3, PDXK, ARAF, TBCD, UBA1, EED, PARVB, RCN2, PGAP3, MED27, PIK3IP1, YTHDF3, BHMT2, ASF1A, ANXA8, ETFA, NMT1, EPHB3, KIF3C, LOH11CR2A (aka VWASA), SLC48A1, MAPKAPK5-AS1, PLA2G4B, CALHM2, SENP5, SIDT2, R3HDM4, MARK4, SSH3, ATOH1, AXIN2, TAS2R13, PCDHB1, VWA7, TRIM49, CNTD2, TSHZ2, CDHR5, KIF26B, *PADI*4, TRIM36, LGI2, KCNMB4, TTTY14, ELAVL3, PAGE4, PER2, ZNF142, CD4, CCS, NELL2, RNF44, KLHL21, DNAJB12, CDC123, GNAI3, TRADD and THRA.

13. The method of claim 5, further comprising a step of measuring the expression level of at least one miRNA, the at least on miRNA selected from the group of hsa-miR-1204, hsa-miR-141-3p, hsa-miR-1827, hsa-miR-938, hsa-miR-125b-5p, hsa-miR-297, hsa-miR-10a-5p, hsa-miR-145-5p, hsa-miR-217, hsa-miR-3185, hsa-miR-21-5p, hsa-miR-363-3p, hsa-miR-631, hsa-miR-655, hsa-miR-1245b-5p, hsa-miR-369-3p, hsa-miR-875-3p, hsa-miR-105-5p, hsa-miR-1253, hsa-miR-1285-3p, hsa-miR-512-5p, hsa-miR-550b-3p, hsa-miR-571 and hsa-miR-935.

14. The method of claim 5, further comprising a step of measuring the expression level of at least one protein, the at least on protein selected from the group of Tectonic-3, DENN domain-containing protein 1A, Proto-oncogene c-Fos, UNC93-like protein MFSD11, Ribose-phosphate pyrophosphokinase 3, Coagulation factor XIII A chain, Kelch-like protein 24, FACT complex subunit SSRP1, ATP-dependent RNA helicase DDX24, Kinesin-like protein KIF1B, Ribosomal RNA-processing protein 7 homolog A, MICAL-like protein 1, UPF0184 protein C9orf16, Selenide, water dikinase 1, ATP synthase subunit s, mitochondrial, Integrin alpha-IIb, Transcriptional activator protein Pur-alpha, Platelet-activating factor acetylhydrolase IB subunit gamma, Pyridoxal kinase, Serine/threonine-protein kinase A-Raf, Tubulin-specific chaperone D, Ubiquitin-like modifier-activating enzyme 1, Polycomb protein EED, Beta-parvin, Reticulocalbin-2, Post-GPI attachment to proteins factor 3, Required for excision 1-B domain-containing protein, Mediator of RNA polymerase II transcription subunit 27, Phosphoinositide-3-kinase-interacting protein 1, YTH domain-containing family protein 3, S-methylmethionine-homocysteine S-methyltransferase BHMT2, Histone chaperone ASF1A, Annexin A8, Electron transfer flavoprotein subunit alpha mitochondrial, Glycylpeptide N-tetradecanoyltransferase 1, Ephrin type-B receptor 3, Kinesin-like protein KIF3C, Loss of heterozygosity, 11, chromosomal region 2, gene A, isoform CRA_b, Heme transporter HRG1, Putative uncharacterized protein encoded by MAPKAPK5-AS1, Cytosolic phospholipase A2 beta, Calcium homeostasis modulator protein 2, Sentrin-specific protease 5, SID1 transmembrane family member 2, R3H domain-containing protein 4, MAP/microtubule affinity-regulating kinase 4, CYSRT1 gene, Protein phosphatase Slingshot homolog 3, Protein atonal homolog 1, Axin-2, Taste receptor type 2 member 13, Protocadherin beta-1, von Willebrand factor A domain-containing protein 7, Tripartite motif-containing protein 49, Cyclin N-terminal domain-containing protein 2, Teashirt homolog 2, hypothetical protein FLJ20251, Cadherin-related family member 5, hypothetical protein FLJ11457, Kinesin-like protein KIF26B, Protein-arginine deiminase type-4, E3 ubiquitin-protein ligase TRIM36, Leucine-rich repeat LGI family member 2, Calcium-activated potassium channel subunit beta-4, ELAV-like protein 3, P antigen family member 4, Period circadian protein homolog 2, Zinc finger protein 142 (Clone pHZ-49), isoform CRA_b, U47924 CD4 molecule, Copper chaperone for superoxide dismutase, Protein kinase C-binding protein NELL2, RING finger protein 44, Kelch-like protein 21, DnaJ homolog subfamily B member 12, Cell division cycle protein 123 homolog, Guanine nucleotide-binding protein G(i) subunit alpha, Tumor necrosis factor receptor type 1-associated DEATH domain protein and Thyroid hormone receptor alpha.

15. The method of claim 1, further comprising a step of identifying a subtype of lung cancer.

16. The method of claim 5, further comprising a step of identifying a subtype of lung cancer.

* * * * *

UNITED STATES PATENT AND TRADEMARK OFFICE
CERTIFICATE OF CORRECTION

| | | |
|---|---|---|
| PATENT NO. | : 11,198,912 B2 | Page 1 of 1 |
| APPLICATION NO. | : 17/003775 | |
| DATED | : December 14, 2021 | |
| INVENTOR(S) | : Patrick Lilley and Martin J. Keiser, III | |

It is certified that error appears in the above-identified patent and that said Letters Patent is hereby corrected as shown below:

On the Title Page

Item (60), under "Related U.S. Application Data," in Column 1, delete "62/902,243" and insert --62/902,943--.

Signed and Sealed this
Twenty-first Day of June, 2022

*Katherine Kelly Vidal*

Katherine Kelly Vidal
*Director of the United States Patent and Trademark Office*